United States Patent [19]

Kirsch

[11] Plant 5,196

[45] Feb. 28, 1984

[54] LILY NAMED FRESCO

[75] Inventor: Ted T. Kirsch, Myrtle Point, Oreg.

[73] Assignee: Sun Valley Bulb Farms, Inc., Myrtle Point, Oreg.

[21] Appl. No.: 422,200

[22] Filed: Sep. 23, 1982

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Chas. W. Rummler

[57] ABSTRACT

A new and distinct Oriental hybrid lily of the Parkmanni type particularly distinguished by its medium sized outwardly facing flowers which have a light pink coloration of both petals and sepals, each of which has a yellow-orange mid-rib, the flowers being borne in a raceme arrangement on long strong stems and stiff outwardly projecting pedicels, there being usually one bud on each pedicel. This plant also has dark glossy green, apparently disease-resistant foliage.

2 Drawing Figures

BACKGROUND OF THE NEW PLANT

This new variety of lily plant originated as a seedling of unknown parentage growing in nursery at Arcata, Calif. and was selected by me for propagation and study because of the attractive arrangement of its pink flowers and its dark green apparently disease-free foliage. Through propagation of this new lily plant for several successive generations by means of scales and tissue culture at Arcata, Calif., I have found advantageous and distinctive characteristics in the new plant which make it particularly suitable for commercial lily cut-flower culture, and continued propagation has shown that its distinctive characteristics hold true from generation to generation and appear to be firmly fixed.

DESCRIPTION OF THE DRAWING

This new lily cultivar is illustrated by the accompanying photographic drawing which in full color shows a full grown blooming plant and a closeup view of one of its blooms, the color rendition being as nearly true as can be obtained by conventional commercial photographic procedures.

DESCRIPTION OF THE NEW PLANT

The following is a detailed description of my new lily cultivar with color designations according to the R.H.S. Colour Chart published by The Royal Horticultural Society of London, England, the observations having been made of field grown plants at Arcata, Calif. in the summer of 1982.

THE PLANT

Origin: Seedling.

Parentage: Unknown.

Classification:

*Botanic.*—Parkmanni type Oriental hybrid.

*Commercial.*—Lily plant for cut flower production.

Form: A tall single stem arising from each single nose bulb.

Height: About 2½ to 3½ feet.

Growth habit: Sturdy and upright with excellent strength.

Cane diameter: From about ¼ inch for a small bulb to about ⅝ inch from a large bulb.

*Color.*—Usually dark red purple with very small oblong light green spots. Base of the cane may be dark green.

Leaves:

*At the flower cluster.*—Number — 1 or 3; there may or may not be one at the base of each pedicel about 3 to 4 inches long and about 1 to 2 inches wide; and one on the pedicel about ½ inch from the flower, about 2¾ inches long and ½ inch to 1 inch wide.

*Shape.*—Lanceolate.

*Texture.*—Leathery.

*Aspect.*—Smooth.

*Ribs and veins.*—There are distinct parallel veins extending from the base of the leaf to the tip.

Bulblets: (On underground stem).

*Occurrence.*—1 to 3 on each healthy, normal plant at digging time.

*Size.*—From about ¼ inch to 1 inch in diameter.

*Color.*—White with occasional pink shading at the tips.

Bulbs:

*Size.*—From about ½ inch to 12 inches in circumference depending upon age.

*Color.*—White, with yellow and pink overtones. As the bulbs become older, the overtones of yellow and pink become more and more prominent.

THE BUD

Form: Generally lanceolate (often almost elliptic) with obtuse apex.

Size: About 4 to 4½ inches long and about 1 to 1¼ inches wide.

Number: Usually 1 on each pedicel with 1 to 10 pedicels on a plant according to culture and bulb size.

Opening rate: Normal. The buds open successively from the lowermost bud to the top bud which is the last to open.

Color: The overall color of the bud is R.H.S. Red 54-D; the basal half having green undertones. The outer half of the bud is redder and the mid-rib at the base of the bud is Red Purple R.H.S. 64-A.

Surface aspect: Rugose and leathery with prominent veins.

Pedicels:

*Character.*—Strong and outwardly projecting.

*Length.*—Relatively short — about 1 to 2 inches long.

*Color.*—Light green on underneath side with some dark red purple coloration at the base. On the top side, dark red purple from the base of the pedicel to the second leaf, then light green, and with numerous light green oblong spots covering the entire pedicel.

THE FLOWER

Blooming habit: This plant blooms annually and profusely in late July when grown outside under normal lily forcing conditions and temperatures.

Size of flower: Medium, about 5 to 6 inches in diameter.

Borne: From larger bulbs, the inflorescence has a raceme arrangement with each pedicel bearing 1 bud. The size of the bulb and its cultural care will determine the number of buds to be found on any given inflorescence. From large bulbs, this lily may have 3 to 6 blooms open at one time.

Shape: The flower is bowl-shaped, with uniformly spaced petals in a star arrangement and with the outer one-third of the petal curving backwardly.

Petalage:

*Number.*—Normal with 3 sepals and 3 petals.

*Form.*—Ovate, with an obtuse apex and a center furrow bisecting each petal longitudinally, the petal edges being slightly undulate at the petal tips.

*Size.*—About 4½ inches long and 2½ inches wide.

*Color.*—(When grown outdoors in Western Coastal states): Upon opening, the flower is generally a light pink, the inner two-thirds of each petal being of Red Purple R.H.S. 62-D to 65-D, the color being lighter toward the base of the petal, darker toward the tip, and covered with numerous red spots of R.H.S. 53-A. The outer third of each petal is more pink, being Red Purple R.H.S. 63-C and having no spots. The mid-rib color of the petals changes from R.H.S. Yellow Green 144-C at the nectary to yellow orange toward the middle third of the petal and then to pink at the tip. The sepals are slightly darker than the petals and have a 1/16 inch off-white R.H.S. 155-C margin around the bottom two-thirds. Under side: Overall R.H.S. Red Purple 65-D, the base being off-white and the outer one-third near the mid-rib being of a more intense pink. The mid-rib is dark red at the base and then becomes slightly redder than the rest of the petal. Also, there is a 1/16 inch wide white margin along the bottom four-fifths of the sepal edge.

*Aspect.*—Velvety.

*Papillae.*—Present at the base of the petals and there being 10 to 20 in number.

Fragrance: Sweet.

Discoloration: The flower darkens and becomes more purple as it ages.

Effect of weather: The flowers of this plant are generally not affected by wet weather, but the flower ages faster as the temperature rises.

Persistence: The flowers tend to hang on and dry.

Lasting quality:

*On the plant.*—2 to 3 weeks depending on size of bulb and its environmental temperature.

*As a cut flower.*—7 to 14 days.

REPRODUCTIVE ORGANS

Stamens: 6 in number and orderly arranged around the pistil.

*Anthers.*—Length: About 1 inch. Color: R.H.S. grade Orange 169-B.

*Filaments.*—Length: About 3¾ inches. Color: White at base becoming light green at the tip.

Pistils: Number — 1.

*Style.*—Length: About 3¼ inches. Color: Light green.

*Stigma.*—Color: Purple.

Character of ovary: Classified as a schizocarp, about 1½ inches long and 1 inch in diameter, dehiscing into thirds and containing 6 rows of seeds of the usual shape for lilies.

I claim:

1. A new and distinct Oriental hybrid lily cultivar substantially as herein shown and described, characterized by its medium pink outwardly facing flowers, the petals of which have a prominent narrow yellow-orange stripe along the mid-rib and numerous maroon spots; and the petal tips are slightly recurved, the flowers are borne on short stiff outwardly projecting pedicels and are long lasting whether on the plant or as a cut flower, and the foliage is dark glossy green and relatively abundant.

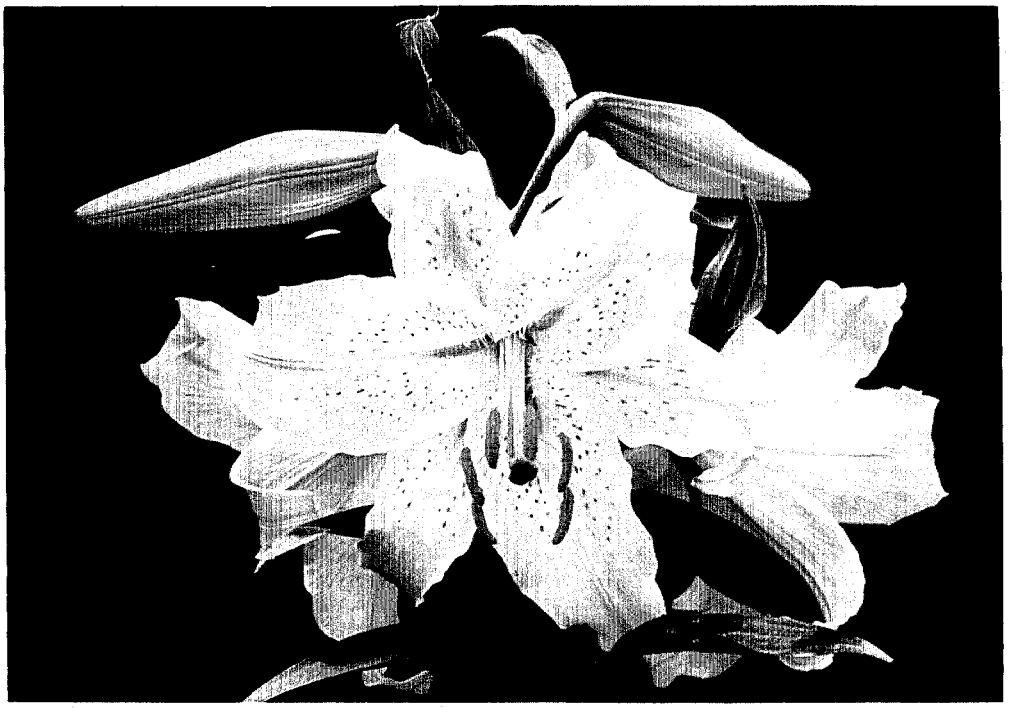
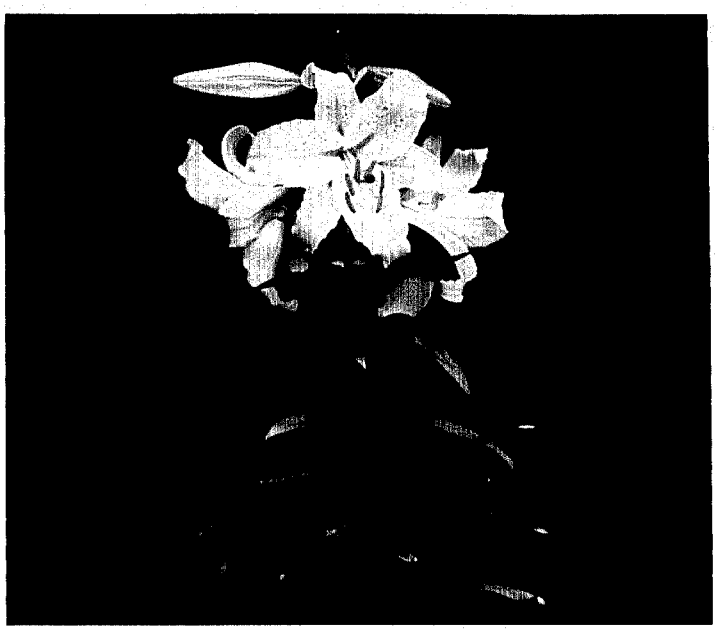

* * * * *